US012059438B2

(12) United States Patent
Cao et al.

(10) Patent No.: US 12,059,438 B2
(45) Date of Patent: Aug. 13, 2024

(54) EYEDROP APPLICABLE TO LIMBAL STEM CELL DEFICIENCY AND PREPARATION

(71) Applicant: QINGDAO HAIER BIOTECH CO., LTD, Qingdao (CN)

(72) Inventors: Qilong Cao, Qingdao (CN); Fei Wang, Qingdao (CN); Hui Li, Qingdao (CN); Guohu Di, Qingdao (CN)

(73) Assignee: QINGDAO HAIER BIOTECH CO., LTD, Qingdao (CN)

( * ) Notice: Subject to any disclaimer, the term of this patent is extended or adjusted under 35 U.S.C. 154(b) by 450 days.

(21) Appl. No.: 17/448,684

(22) Filed: Sep. 23, 2021

(65) Prior Publication Data
US 2022/0008478 A1    Jan. 13, 2022

Related U.S. Application Data

(63) Continuation of application No. PCT/CN2021/073682, filed on Jan. 26, 2021.

(51) Int. Cl.
| A61K 31/00 | (2006.01) |
| A61K 9/00 | (2006.01) |
| A61K 35/28 | (2015.01) |
| A61K 47/18 | (2017.01) |
| A61K 47/24 | (2006.01) |
| A61K 47/36 | (2006.01) |
| C12N 5/0775 | (2010.01) |

(52) U.S. Cl.
CPC ............ *A61K 35/28* (2013.01); *A61K 9/0048* (2013.01); *A61K 47/186* (2013.01); *A61K 47/24* (2013.01); *A61K 47/36* (2013.01); *C12N 5/0667* (2013.01); *C12N 2509/00* (2013.01)

(58) Field of Classification Search
CPC ....................................................... A61K 31/00
See application file for complete search history.

(56) References Cited

PUBLICATIONS

English machine translation of Gao et al., CN 110279893 A, Sep. 2019.*

* cited by examiner

*Primary Examiner* — Rosanne Kosson
(74) *Attorney, Agent, or Firm* — CBM PATENT CONSULTING, LLC

(57) ABSTRACT

The present disclosure relates to an eyedrop applicable to limbal stem cell deficiency and a preparation method, wherein each liter of the eyedrop includes the following components: 1 to 40 mg of human adipose-derived stem cell exosomes, excipients: 0.5 to 2 g of sodium hyaluronate, 0.5 to 3 g of vitamin B6 and 0.05 to 0.3 g of benzalkonium chloride, and the balance of medical normal saline, a pH of the eyedrop is 6.5 to 7.5; and the eyedrop of the present disclosure is effective in treating limbal stem cell deficiency.

12 Claims, 3 Drawing Sheets

EYEDROP APPLICABLE TO LIMBAL STEM CELL DEFICIENCY AND PREPARATION

CROSS REFERENCES

This application is the U.S. continuation application of International Application No. PCT/CN2021/073682 filed on 26 Jan. 2021 which designated the U.S. and claims priority to Chinese Application No. 202010496058.5 filed on 3 Jun. 2020, the entire contents of each of which are hereby incorporated by reference.

FIELD OF THE INVENTION

The present disclosure belongs to the technical field of medicines, and in particular, relates to an eyedrop applicable to limbal stem cell deficiency and a preparation method.

BACKGROUND OF THE INVENTION

Limbal stem cells are a group of stem cells located at the limbal palisades of Vogt. Limbal stem cells proliferate and differentiate continuously to maintain the stability and renewal of the corneal epithelium. A chemical damage or thermal burn to the ocular surface, dry eyes, long-term wearing of corneal contact lenses (contact lenses) and other factors may cause decompensation of the number and function of limbal stem cells, thereby leading to limbal stem cell deficiency. The limbal stem cell deficiency causes the corneal epithelium to lose its ability to regenerate and repair, which results in corneal epithelialization, neovascularization, corneal stroma scarring, and even corneal autolysis and ulceration. The limbal stem cell deficiency is a common blinding eye disease in China and other developing countries, and mostly occurs in young and middle-aged working people, which causes serious economic and spiritual burdens to patients' families and society.

Currently, common therapies for treating the limbal stem cell deficiency are autologous/allogeneic limbus transplantation, allogeneic limbal stem cell transplantation, in vitro cultured oral mucosal cell transplantation, amniotic membrane transplantation, etc. Although these methods have achieved certain clinical effects, there are still many defects, for example, the limbus transplantation will produce a rejection action, the limbal stem cells are difficult to proliferate and easy to differentiate in vitro, the oral mucosal cell transplantation has poor biological effects, and the amniotic membrane transplantation cannot repair corneal epithelium.

The Chinese patent document CN109449770A (application number: 201810188801.3) discloses a mesenchymal stem cell exosome eyedrop and a preparation method and application thereof, and discloses a mesenchymal stem cell exosome eyedrop with a pH of 5.2 to 6.0 and an osmotic pressure of 0.24 to 0.36 mOsm/L, each 1,000 mL includes 1.5 to 2.5 g of taurine, 0.12 to 0.16 g of natural borneol, 1.5 to 2.5 mL of medicinal ethanol, 8 to 12 mg of mesenchymal stem cell exosomes, appropriate amount of glycerol and appropriate amount of disodium hydrogen phosphate, medical normal saline serves a solvent; sources of the mesenchymal stem cell exosomes includes umbilical cord mesenchymal stem cells, adipose-derived mesenchymal stem cells and placental mesenchymal stem cells; the mesenchyme stem cells are planted in a culture flask after being subcultured for at least 3 times, the culture flask is replaced with a serum-free growth medium when 75% to 85% of the cells are fused, the medium is collected after the cells are continued to be cultured for at least 3 d, and then a stem cell exosome suspension is obtained by using an exosome extraction kit; the disclosure shows that the eyedrop has health care functions of relieving asthenopia, reducing intraocular pressure and eliminating eye congestion, and has a certain preventive and therapeutic effect on eye diseases such as myopia, hyperopia, presbyopia, glaucoma, cataracts, age-related macular degeneration.

The Chinese patent document CN108743620A (application number: 201810643146.6) discloses a bioactive material promoting stem cell-derived exosomes to treat a corneal damage. According to the disclosure, exosomes secreted by stem cells are combined with a bioactive material hydrogel by physical mixing, the exosomes are released into the surrounding tissues, and its release speed and release mode are regulated; the hydrogel is a bioactive material hydrogel eyedrop, the hydrogel has the physical and chemical properties of the biological material and also has the biological activity of the secretion of stem cells. The biological material may be chitosan, hyaluronic acid, sodium carboxymethyl cellulose and other materials that may be used for ocular administration; the exosomes are stem cell-derived exosomes, the stem cells include adipose-derived mesenchymal stem cells, bone marrow mesenchymal stem cells, umbilical cord mesenchymal stem cells, placental mesenchymal stem cells, urine-derived stem cells, endothelial progenitor cells or cardiac stem cells, etc.; the disclosure shows that the hydrogel eyedrop may effectively enhance the retention rate of the exosomes at a damaged site, at the same time improve the stability of effective components such as protein and microRNA of the exosomes, slowly release the exosomes to the damaged site, further improve the therapeutic effect of the exosomes, and promote the recovery of the damaged tissue structure and function.

Currently, there are few reports about applications of exosome components extracted by using a stem cell growth medium in corneal damage repair and alleviation of visual fatigue. However, an application of an eyedrop prepared by using human adipose-derived stem cell exosomes in limbal stem cell deficiency, especially in an effective prevention of secondary corneal neovascularization and corneal epithelial conjunctivation has not been reported.

SUMMARY OF THE INVENTION

Aiming at the defects in the prior art, the present disclosure provides an eyedrop applicable to limbal stem cell deficiency and a preparation method.

The eyedrop of the present disclosure is applicable to limbal stem cell deficiency caused by multiple factors.

Technical Solutions of the Present Disclosure

An application of human adipose-derived stem cell exosomes serving as effective components in preparation of a medicine for treating limbal stem cell deficiency.

A medicine for treating limbal stem cell deficiency, including human adipose-derived stem cell exosomes.

An application of a composite serving as an effective component in preparation of a medicine for treating limbal stem cell deficiency, the composite including the following components: human adipose-derived stem cell exosomes, excipients: sodium hyaluronate, vitamin B6 and benzalkonium chloride, and medical normal saline.

According to the present disclosure, preferably, each liter of the composite includes the following components: 1 to 40 mg of the human adipose-derived stem cell exosomes, and the excipients: 0.5 to 2 g of the sodium hyaluronate, 0.5 to 3 g of the vitamin B6 and 0.05 to 0.3 g of the benzalkonium chloride.

According to the present disclosure, preferably, each liter of the composite includes the following components: 20 mg of the human adipose-derived stem cell exosomes, the excipients: 2 g of the sodium hyaluronate, 3 g of the vitamin B6 and 0.3 g of the benzalkonium chloride, and the medical normal saline.

A medicine for treating limbal stem cell deficiency, including human adipose-derived stem cell exosomes, excipients: sodium hyaluronate, vitamin B6 and benzalkonium chloride, and medical normal saline.

According to the present disclosure, preferably, each liter of the medicine includes 1 to 40 mg of the human adipose-derived stem cell exosomes, the excipients: 0.5 to 2 g of the sodium hyaluronate, 0.5 to 3 g of the vitamin B6 and 0.05 to 0.3 g of the benzalkonium chloride, and the medical normal saline.

Further preferably, each liter of the medicine includes 20 mg of the human adipose-derived stem cell exosomes, the excipients: 2 g of the sodium hyaluronate, 3 g of the vitamin B6 and 0.3 g of the benzalkonium chloride, and the medical normal saline.

An eyedrop applicable to limbal stem cell deficiency, including the following components per liter: 1 to 40 mg of human adipose-derived stem cell exosomes, excipients: 0.5 to 2 g of sodium hyaluronate, 0.5 to 3 g of vitamin B6 and 0.05 to 0.3 g of benzalkonium chloride, and the balance of medical normal saline, a pH of the eyedrop being 6.5 to 7.5.

An osmotic pressure of the eyedrop is 310 to 315 mOSm/L.

According to the present disclosure, preferably, each liter of the eyedrop includes the following components: 20 mg of the human adipose-derived stem cell exosomes, the excipients: 2 g of the sodium hyaluronate, 3 g of the vitamin B6 and 0.3 g of the benzalkonium chloride, and the balance of the medical normal saline, and the pH of the eyedrop is 6.5 to 7.5.

According to the present disclosure, preferably, the above medical normal saline is normal saline for injection.

A preparation method of the above eyedrop applicable to limbal stem cell deficiency, including the following steps:
(1) selecting human adipose-derived stem cells which are subcultured for 3 to 5 times, culturing the cells by using a stem cell growth medium until 70% to 80% of the cells are fused, replacing the stem cell growth medium with a stem cell serum-free growth medium, continuing to culture the stem cells for 36 to 48 h, collecting a supernatant, extracting human adipose-derived stem cell exosomes, and resuspending the exosomes to prepare a human adipose-derived stem cell exosome solution; and
(2) uniformly mixing the human adipose-derived stem cell exosome solution prepared at step (1) with other components according to the concentration of the exosome components of the above eyedrop, and adjusting a pH of the mixture to be 6.5 to 7.5 to prepare the eyedrop.

According to the present disclosure, preferably, at step (1) the exosomes are extracted by means of gradient ultracentrifugation that is performed under the following specifically selected centrifugal forces in sequence: the centrifugation is performed under 300×g for 20 min, and a supernatant is retained; the centrifugation is performed under 10,000×g for 30 min, and a supernatant is retained; the centrifugation is performed under 100,000×g for 1 h, a supernatant is removed, and precipitates are retained and serve as the human adipose-derived stem cell exosomes.

Further preferably, at step (1) the human adipose-derived stem cell exosomes are resuspended by using an HBSS.

According to the present disclosure, preferably, at step (1) the protein content of the resuspended exosomes is measured by means of BCA, that is, the concentration of the human adipose-derived stem cell exosomes, the use concentration of the exosomes is adjusted to prepare the human adipose-derived stem cell exosome solution.

According to the present disclosure, preferably, at step (2) sodium hyaluronate is dissolved in medical normal saline according to the components of the above eyedrop, and then vitamin B6 and benzalkonium chloride at corresponding concentration are dissolved in the mixture in sequence, a pH of the mixture is adjusted to be 6.5 to 7.5, the human adipose-derived stem cell exosome solution prepared at step (1) at corresponding concentration is added to the mixture, and the mixture is uniformly mixed to prepare the eyedrop.

According to the present disclosure, preferably, at step (2) the pH is adjusted to be 6.5 to 7.5 by using HCl and/or NaOH.

According to the present disclosure, preferably, each liter of the eyedrop prepared at step (2) includes the following components: 20 mg of the human adipose-derived stem cell exosomes, the excipients: 2 g of the sodium hyaluronate, 3 g of the vitamin B6 and 0.3 g of the benzalkonium chloride, and the balance of the medical normal saline, and the pH of the eyedrop is 6.5 to 7.5.

According to the present disclosure, preferably, in the components of the eyedrop prepared at step (2), the medical normal saline is normal saline for injection.

An application of the eyedrop to limbal stem cell deficiency caused by a chemical injury or thermal burn to an eye, or other reasons.

Beneficial Effects of the Technical Solutions of the Present Disclosure

Compared to the prior art, the present disclosure has the following advantages:
1. The eyedrop of the present disclosure is applicable to limbal stem cell deficiency, and especially has a significant application effect on effective prevention of symptoms of secondary corneal neovascularization and corneal epithelial conjunctivitation.
2. Compared to stem cell transplantation, amniotic membrane transplantation, oral mucosal cell transplantation, etc., the stem cell exosome eyedrop of the present disclosure has the advantages of simple preparation, simple operation, and low technical difficulty.
3. The stem cell exosome eyedrop of the present disclosure includes a variety of active substances, has good stability and biological activity, and has a sustained-release effect, which is conducive to safe and effective local eye treatment.
4. The eyedrop of the present disclosure is convenient to carry, and low in cost, which reduces the economic burden of users.

Figure 2:
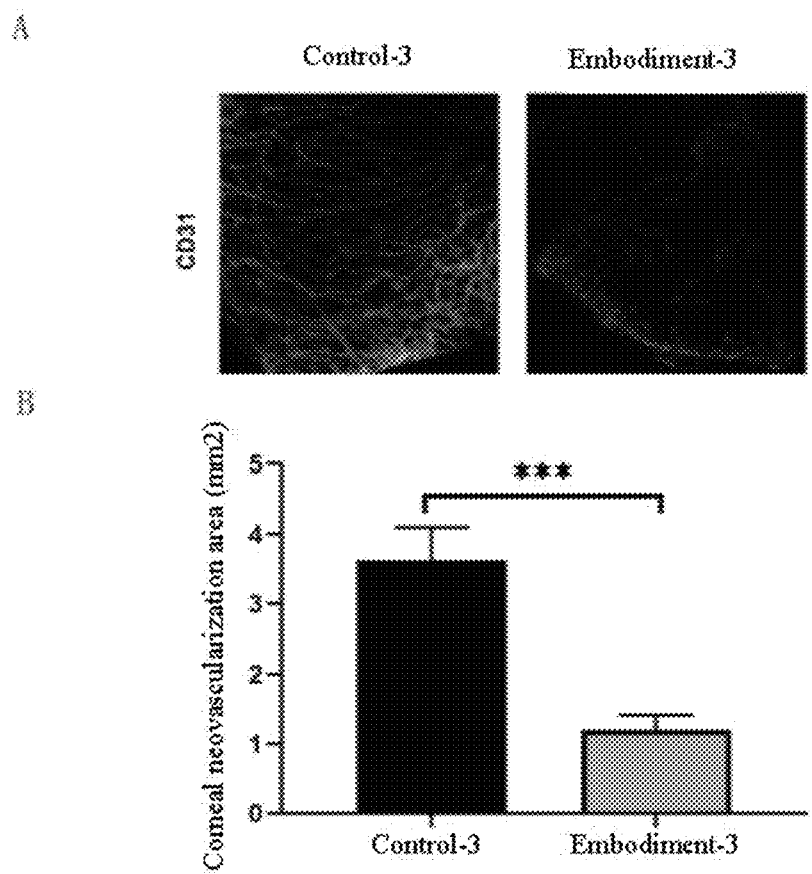
Figure 3:
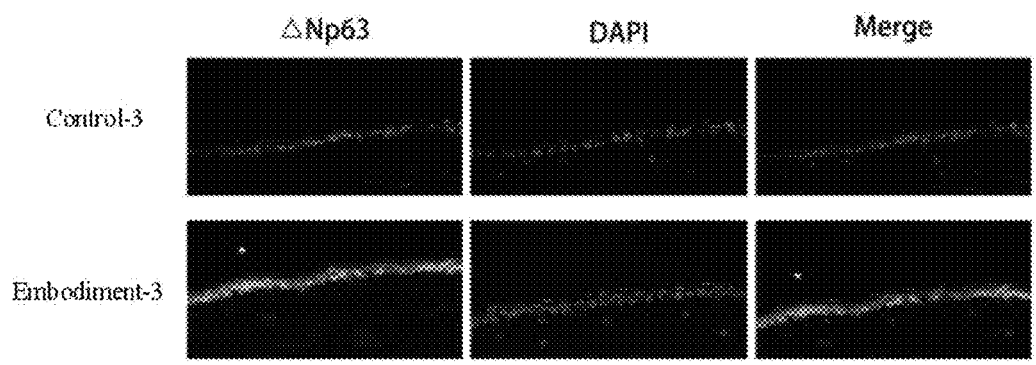
Figure 4:
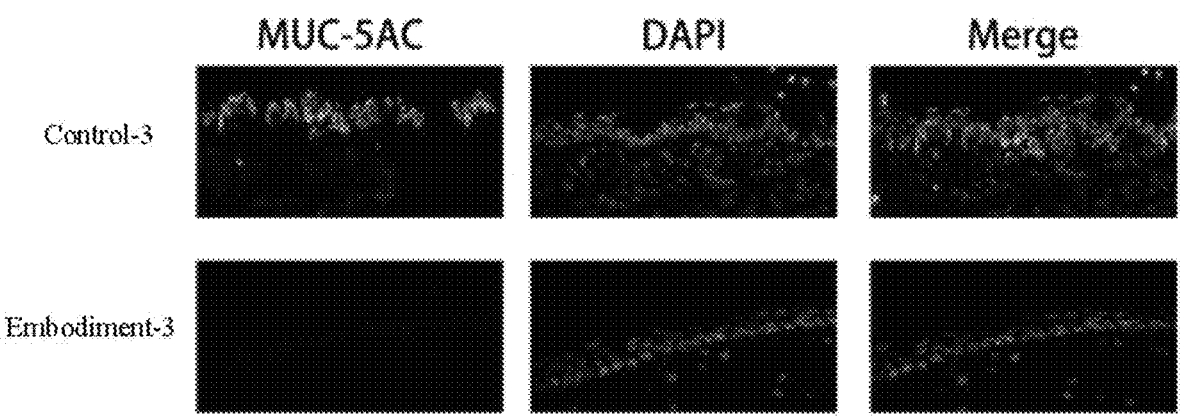

wherein A shows the slit-lamp photos; and B shows the corneal clinical score statistical diagram;

FIG. 2 shows diagrams of stretched preparation of the mouse corneas subjected to immunofluorescence staining using a neovascularization marker CD31 and a corneal neovascularization area statistical diagram after the mouse limbal stem cell deficiency animal models are treated by the eyedrops prepared in Embodiment-3 and Control-3 for 28 days;

wherein A shows the CD31 immunofluorescence staining photos of the corneal neovascularization; and B shows the corneal neovascularization area statistical diagram;

FIG. 3 shows photos of frozen sections of the mouse corneas subjected to immunofluorescence staining using a limbal stem cell maker ΔNp63 and subjected to immunofluorescence staining using a cell nucleus stainer DAPI, and photos of the two kinds of immunofluorescence staining photos processed by means of Merge after the mouse limbal stem cell deficiency animal models are treated by the eyedrops prepared in Embodiment-3 and Control-3 for 28 days; and FIG. 4 shows photos of frozen sections of the mouse corneas subjected to immunofluorescence staining using a conjunctival goblet cell maker MUC-5AC and subjected to immunofluorescence staining using the cell nucleus stainer DAPI, and photos of the two kinds of immunofluorescence staining photos processed by means of Merge after the mouse limbal stem cell deficiency animal models are treated by the eyedrops prepared in Embodiment-3 and Control-3 for 28 days.

DETAILED DESCRIPTION OF THE EMBODIMENTS

The present disclosure will be further described below in conjunction with embodiments, but the scope of protection is not limited thereto.

The contents of the embodiments without indicating specific conditions are performed according to conventional conditions; and the used reagents or instruments without indicating manufacturers are all common commercial products.

Sources of Main Materials

Human adipose-derived stem cells: separated from fats obtained by performing liposuction on a healthy adult female (20 to 30 years old); or existing commercially available human adipose stem cells;
  sodium hyaluronate: purchased from Sigma Company;
  vitamin B6: purchased from Sigma Company;
  benzalkonium chloride: purchased from Sigma Company;
  MEM adipose-derived stem cell basic growth media: purchased from Thermofisher Company;
  Stem cell growth media: purchased from Cyagen (Guangzhou) Bioscience Co., Ltd.;
  HBSS: purchased from Thermofisher Company;
  human placental stem cells: separated from a placenta of a healthy full-term fetus; or existing commercially available human placental stem cells; and
  human umbilical cord stem cells: separated from an umbilical cord of a healthy full-term fetus; or existing commercially available human umbilical cord stem cells.

Embodiment 1

Each liter of an eyedrop applicable to limbal stem cell deficiency included the following components:

1 mg of the human adipose-derived stem cell exosomes, excipients: 0.5 g of the sodium hyaluronate, 1 g of the vitamin B6 and 0.05 g of the benzalkonium chloride, and the balance of normal saline for injection, and a pH of the eyedrop was 7.0.

A preparation method of the above eyedrop included the following steps:
  (1) preparation of human adipose-derived stem cell exosomes: third-generation human adipose-derived stem cells were selected and were cultured in a thermostatic cell incubator with $CO_2$ at volume concentration of 5% at 37° C. by using a stem cell growth medium until 80% of the cells were fused, the cells were cultured by using an MEM stem cell basic growth medium instead of the stem cell growth medium for 48 h and cultured in the thermostatic cell incubator with $CO_2$ at volume concentration of 5% at 37° C., a culture supernatant was collected, exosomes were extracted by means of gradient ultracentrifugation which was performed under the following selected centrifugal forces in sequence: the centrifugation was performed under 300×g for 20 min, a supernatant was retained; the centrifugation was performed under 10,000×g for 30 min, a supernatant was retained; the centrifugation was performed under 100,000×g for 1 h, a supernatant was removed, precipitates were retained and served as the human adipose-derived stem cell exosomes, the exosomes were resuspended by using an HBSS, the protein content of the resuspended exosomes was measured by using a BCA kit, that is, the concentration of the human adipose-derived stem cell exosomes, and the use concentration of the exosomes was adjusted to prepare a human adipose-derived stem cell exosome solution; and
  (2) the sodium hyaluronate was dissolved in the normal saline for injection according to the components of the above eyedrop, and then the vitamin B6 and the benzalkonium chloride were dissolved in the mixture in sequence, a pH of the mixture was adjusted to be 7.0 by using HCl and NaOH, corresponding amount of the human adipose-derived stem cell exosome solution prepared at step (1) was added to the mixture to enable the concentration of the exosomes in the final solution to be 1 mg/L, so as to prepare the above eyedrop.

An osmotic pressure of the eyedrop was 312 mOSm/L.

Embodiment 2

Each liter of an eyedrop applicable to limbal stem cell deficiency included the following components:

10 mg of the human adipose-derived stem cell exosomes, the excipients: 1 g of the sodium hyaluronate, 2 g of the vitamin B6 and 0.1 g of the benzalkonium chloride, and the balance of normal saline for injection, and a pH of the eyedrop was 7.0.

A preparation method of the above eyedrop included the following steps:
  (1) preparation of human adipose-derived stem cell exosomes: third-generation human adipose-derived stem cells were selected and were cultured in a thermostatic cell incubator with $CO_2$ at volume concentration of 5% at 37° C. by using a stem cell growth medium until 80% of the cells were fused, the cells were cultured by using an MEM stem cell basic growth medium instead of the stem cell growth medium for 48 h and cultured in the thermostatic cell incubator with $CO_2$ at volume concentration of 5% at 37° C., a culture supernatant was collected, exosomes were extracted by means of gradient ultracentrifugation which was performed under the following selected centrifugal forces in sequence: the centrifugation was performed under 300×g for 20 min, a supernatant was retained; the centrifugation was performed under 10,000×g for 30 min, a supernatant was retained; the centrifugation was performed under 100,000×g for 1 h, a supernatant was removed, precipitates were retained and served as the human adipose-derived stem cell exosomes, the exosomes were resuspended by using an HBSS, the protein content of the resuspended exosomes was measured by using a BCA kit, that is, the concentration of the human adipose-derived stem cell exosomes, and the use concentration of the exosomes was adjusted to prepare a human adipose-derived stem cell exosome solution; and (2) the sodium hyaluronate was dissolved in the normal saline for injection according to the components of the above eyedrop, and then the vitamin B6 and the benzalkonium chloride were dissolved in the mixture in sequence, a pH of the mixture was adjusted to be 7.0 by using HCl and NaOH, corresponding amount of the human adipose-derived stem cell exosome solution prepared at step (1) was added to the mixture to enable the concentration of the exosomes in the final solution to be 10 mg/L, so as to prepare the above eyedrop.

An osmotic pressure of the eyedrop was 312 mOSm/L.

Embodiment 3

Each liter of an eyedrop applicable to limbal stem cell deficiency included the following components:

20 mg of the human adipose-derived stem cell exosomes, excipients: 2 g of the sodium hyaluronate, 3 g of the vitamin B6 and 0.3 g of the benzalkonium chloride, and the balance of normal saline for injection.

A preparation method of the above eyedrop included the following steps:

(1) preparation of human adipose-derived stem cell exosomes: fourth-generation human adipose-derived stem cells were selected and were cultured in a thermostatic cell incubator with $CO_2$ at volume concentration of 5% at 37° C. by using a stem cell growth medium until 80% of the cells were fused, the cells were cultured by using an MEM stem cell basic growth medium instead of the stem cell growth medium for 48 h and cultured in the thermostatic cell incubator with $CO_2$ at volume concentration of 5% at 37° C., a culture supernatant was collected, exosomes were extracted by means of gradient ultracentrifugation which was performed under the following selected centrifugal forces in sequence: the centrifugation was performed under 300×g for 20 min, a supernatant was retained; the centrifugation was performed under 10,000×g for 30 min, a supernatant was retained; the centrifugation was performed under 100,000×g for 1 h, a supernatant was removed, precipitates were retained and served as the human adipose-derived stem cell exosomes, the exosomes were resuspended by using an HBSS, the protein content of the resuspended exosomes was measured by using a BCA kit, that is, the concentration of the human adipose-derived stem cell exosomes, and the use concentration of the exosomes was adjusted to prepare a human adipose-derived stem cell exosome solution; and (2) the sodium hyaluronate was dissolved in the normal saline for injection according to the components of the above eyedrop, and then the vitamin B6 and the benzalkonium chloride were dissolved in the mixture in sequence, a pH of the mixture was adjusted to be 7.0 by using HCl and NaOH, corresponding amount of the human adipose-derived stem cell exosome solution prepared at step (1) was added to the mixture to enable the concentration of the exosomes in the final solution to be 20 mg/L, so as to prepare the above eyedrop.

An osmotic pressure of the eyedrop was 312 mOSm/L.

Control 1

A difference from the eyedrop of Embodiment 1 is that the human adipose stem cell exosomes in the components of the eyedrop were cultured by using an MEM adipose-derived stem cell basic growth medium, and the others were the same.

Control 2

A difference from the eyedrop of Embodiment 2 is that the human adipose stem cell exosomes in the components of the eyedrop were replaced with human placental stem cell exosomes at the same concentration of 10 mg/L in the eyedrop, a preparation method of the human placental stem cell exosomes was the same as that of the human adipose-derived stem cell exosomes, and the others were the same.

Control 3

A difference from the eyedrop of Embodiment 3 is that the human adipose stem cell exosomes in the components of the eyedrop were replaced with human umbilical cord stem cell exosomes at the same concentration of 20 mg/L in the eyedrop, a preparation method of the human umbilical cord stem cell exosomes was the same as that of the human adipose-derived stem cell exosomes, and the others were the same.

Effect Cases

Figure 1:
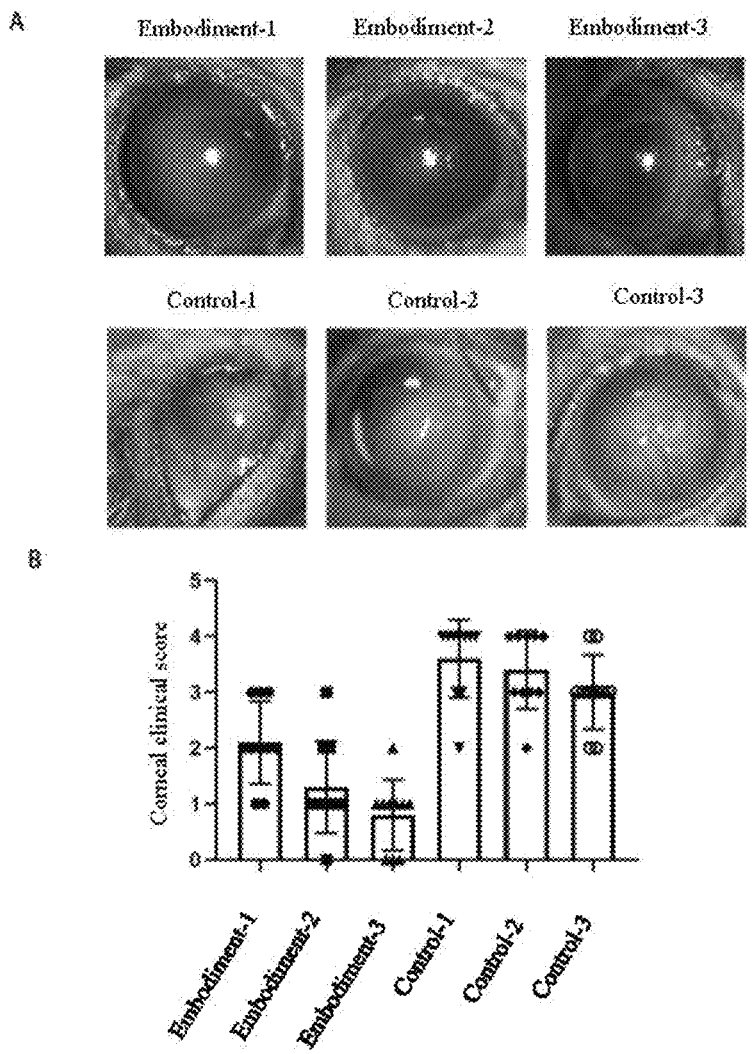
FIG. 1 shows mouse eyeball slit-lamp photos and a clinical score statistical diagram after mouse limbal stem cell deficiency animal models are treated by eyedrops prepared in Embodiments 1 to 3 and Controls 1 to 3 for 28 days.

Referring to *Reconstruction of chemically burned rat corneal surface by bone marrow-derived human mesenchymal stem cells*, Stem Cells, 2006 February; 24(2): 315-21, mouse limbal stem cell deficiency models were constructed by means of filter paper ring. After the mouse models were constructed, the above eyedrops were respectively put into eyes of the mouse models 4 times a day at 8:00 AM, 11:00 AM, 14:00 PM and 17:00 PM according to a dose of 5 ul/eye/time for 28 days. After being treated by the eyedrops prepared in Embodiments 1 to 3 and Controls 1 to 3, mouse eyeballs were photographed under a slit-lamp, mouse corneal clinical scores were analyzed, mouse corneal neovascularization was stained by using a CD31 antibody, frozen sections of the mouse corneas were stained using a limbal stem cell marker ΔNp63 antibody, subjected to immunofluorescent staining using a conjunctival goblet cell marker MUC-5AC, and subjected to immunofluorescent staining using a cell nucleus stainer DAPI. Detection indicators related to limbal stem cell deficiency of mice were improved significantly, and test results are shown in FIG. 1, FIG. 2, FIG. 3, and FIG. 4:

FIG. 1 shows mouse eyeball slit-lamp photos and a clinical score statistical diagram of the mouse limbal stem cell deficiency animal models treated by the eyedrops prepared in Embodiments 1 to 3 and Controls 1 to 3 for 28 days. A denotes the slit-lamp photos which show that mouse corneas of Controls 1 to 3 showed varying degrees of turbidity, and were accompanied by neovascularization; and compared to Controls 1 to 3, the turbidity of mouse corneas of Embodiments 1 to 3 was reduced; and B denotes the corneal clinical score statistics which shows that compared to Controls 1 to 3, the mouse corneal clinical scores of Embodiments 1 to 3 were significantly improved. The corneal clinical score statistics was performed by referring to a scoring system in a classical document which is *Mesenchymal Stromal Cells Inhibit Inflammatory Lymphangiogenesis in the Cornea by Suppressing Macrophage in a TSG-6-Dependent Manner*, Mol Ther 26, 162-172, doi: 10.1016/j.ymthe.2017.09.026 (2018).

It can be seen from FIG. 1 that compared to the eyedrops prepared in Controls 1 to 3, the eyedrops prepared in Embodiments 1 to 3 all had treatment effects, and Embodiment-3 had the best treatment effect.

FIG. 2 shows diagrams of stretched preparation of the mouse corneas treated by the eyedrops prepared in Embodiment-3 and Control-3 subjected to CD31 corneal neovascularization staining after the mouse limbal stem cell deficiency animal models are treated by the eyedrops prepared in Embodiments-3 and Controls-3 for 28 days. In the figure: A denotes CD31 immunofluorescent staining photos of the corneal neovascularization and results show that there was a large number of neovascularization in the mouse cornea of Control 3, but the neovascularization of the mouse corneal of Embodiment-3 was significantly reduced; and B is a corneal neovascularization area statistical diagram and results show that compared to Control-3, the neovascularization area of the mouse cornea of Embodiment 3 was significantly reduced; and a statistical method referred to: *Effects of mesenchymal stem/stromal cells on cultures of corneal epithelial progenitor cells with ethanol injury*, Invest Ophthalmol Vis Sci 55, 7628-7635, doi: 10.1167/iovs. 14-15424 (2014).

Corneal neovascularization is an important indicator of limbal stem cell deficiency, and it can be seen from FIG. 2 that compared to the group treated by the eyedrop prepared in Control-3, the mouse corneal neovascularization of the group treated by the eyedrop prepared in Embodiment-3 was significantly reduced.

FIG. 3 shows diagrams of frozen sections of the mouse corneas treated by the eyedrops prepared in Embodiment-3 and Control-3 subjected to immunofluorescent staining using a limbal stem cell marker ΔNp63 and a cell nucleus stainer DAPI after the mouse limbal stem cell deficiency animal models are treated by the eyedrops prepared in Embodiments-3 and Controls-3 for 28 days. The figure shows ΔNp63 immunofluorescent staining photos, DAPI immunofluorescent staining photos, and photos of the two kinds of immunofluorescent staining photos processed by means of Merge. ΔNp63 is a limbal stem cell marker, and decrease or loss of ΔNp63 positive cells is an important indicator of limbal stem cell deficiency according to *Therapeutic Effect of Human Adipose Tissue-Derived Mesenchymal Stem Cells in Experimental Corneal Failure Due to Limbal Stem Cell Niche Damage*, Stem Cells 35, 2160-2174, doi: 10.1002/stem. 2672 (2017).

It can be seen from FIG. 3 that limbal stem cells of the mouse treated by the eyedrop prepared in Control-3 basically disappeared, but compared to Control-3, the number of limbal stem cells of the mouse treated by the eyedrop prepared in Embodiment-3 significantly increased.

FIG. 4 shows diagrams of frozen sections of the mouse corneas treated by the eyedrops prepared in Embodiment-3 and Control-3 subjected to immunofluorescent staining using a conjunctival goblet cell marker MUC-5AC and the cell nucleus stainer DAPI after the mouse limbal stem cell deficiency animal models are treated by the eyedrops prepared in Embodiments-3 and Controls-3 for 28 days. The figure shows MUC-5AC immunofluorescent staining photos, DAPI immunofluorescent staining photos, and photos of the two kinds of immunofluorescent staining photos processed by means of Merge. MUC-5AC is a conjunctival goblet cell marker, and conjunctival goblet cell infiltration is an important indicator of limbal stem cell deficiency according to *A Simple Mechanical Procedure to Create Limbal Stem Cell Deficiency in Mouse*, J Vis Exp, doi: 10.3791/54658 (2016).

It can be seen from FIG. 4 that the mouse cornea treated by the eyedrop prepared in Control-3 had the conjunctival goblet cell infiltration, but compared to Control-3, the mouse in the treatment group of the eyedrop prepared in Embodiment-3 had complete cornea without conjunctival goblet cells.

Result Analysis

The above results prove that after being constructed, the mouse limbal stem cell deficiency models which were administered with stem cell basic growth medium+excipients (Control −1), with human placental stem cell exosomes+excipients (Control −2), and with human umbilical cord stem cell exocrine exosomes+excipients (Control −3), that is, treated by the eyedrops prepared in Controls 1 to 3 all showed severe limbal stem cell deficiency. The specific manifestations are as follows: the mouse cornea was severely cloudy, neovascularization invaded the cornea, the limbal stem cells disappeared significantly, and the conjunctival goblet cells invaded the cornea. However, after the mouse models were administered with the eyedrops including the human adipose-derived stem cell exosomes of the present disclosure (Embodiments 1, 2 and 3), significant treatment effect was showed, which indicates that the components of the eyedrop of the present disclosure have certain specificity, and may effectively treat limbal stem cell deficiency.

The above is only a description of the specific implementations of the present disclosure. It should be noted that the present disclosure is not limited to the specific implementations described above. Any simple modification and improvement made based on the technical essence of the present disclosure without departing from the scope of the technical solutions of the present disclosure shall fall within the scope of protection of the technical solutions of the present disclosure.

What is claimed is:

1. A composition for treating limbal stem cell deficiency, comprising
   (a) human adipose-derived stem cell exosomes;
   (b) sodium hyaluronate;
   (c) vitamin B6;
   (d) benzalkonium chloride; and
   (e) medical normal saline solution, wherein each liter of the composition comprises the following components: 1 to 40 mg of the human adipose-derived stem cell exosomes, 0.5 to 2 g of the sodium hyaluronate, 0.5 to 3 g of the vitamin B6, 0.05 to 0.3 g of the benzalkonium chloride, and the remainder as the medical normal saline solution.

2. The composition according to claim 1, wherein each liter of the composition comprises the following components: 20 mg of the human adipose-derived stem cell exosomes, 2 g of the sodium hyaluronate, 3 g of the vitamin B6, 0.3 g of the benzalkonium chloride, and the remainder as the medical normal saline solution.

3. The composition according to claim 1, wherein the composition is prepared as an eyedrop.

4. The composition according to claim 2, wherein the composition is prepared as an eyedrop.

5. The composition according to claim 1, wherein the medical normal saline solution is normal saline for injection.

6. A method for preparing the composition of claim 1, wherein the composition is an eyedrop, comprising the following steps:
  (1) selecting human adipose-derived stem cells which are subcultured for 3 to 5 times, culturing the cells by using a stem cell growth medium until the stem cells are 70% to 80% confluent,
  replacing the stem cell growth medium with a stem cell serum-free growth medium,
  continuing to culture the stem cells for 36 to 48 h,
  collecting a supernatant,
  extracting the human adipose-derived stem cell exosomes, and
  resuspending the human adipose-derived stem cell exosomes; and
  (2) adjusting the human adipose-derived stem cell exosomes prepared at step (1) to a desired concentration, and
  adjusting a pH between 6.5 and to 7.5 to yield the eyedrop.

7. The method according to claim 6, characterized in that at step (1) the exosomes are extracted by means of gradient ultracentrifugation which is performed under the following specifically selected centrifugal forces in sequence: the centrifugation is performed under 300×g for 20 min, and a supernatant is retained; the centrifugation is performed under 10,000×g for 30 min, and a supernatant is retained; the centrifugation is performed under 100,000×g for 1 h, a supernatant is removed, and precipitates are retained and serve as the human adipose-derived stem cell exosomes.

8. The method according to claim 6, wherein the human adipose-derived stem cell exosomes are resuspended in Hank's Balanced Salt Solution (HBSS).

9. The method according to claim 6, wherein the protein content of the resuspended exosomes is measured by the bicinchoninic protein assay (BCA) protocol for adjusting to amount of the human adipose-derived stem cell exosomes in the eyedrop.

10. The method according claim 6, wherein at step (2) the sodium hyaluronate is dissolved in the medical normal saline solution, the vitamin B6 and benzalkonium chloride are dissolved in the mixture in sequence, the pH is adjusted to a value between 6.5 and 7.5, and the human adipose-derived stem cell exosomes from step (1) are added.

11. The method according claim 10, wherein the pH is adjusted with HCl and/or NaOH; and the medical normal saline solution is normal saline for injection.

12. The method according claim 6, wherein each liter of the eyedrop prepared at step (2) comprises 20 mg of the human adipose-derived stem cell exosomes, 2 g of the sodium hyaluronate, 3 g of the vitamin B6, 0.3 g of the benzalkonium chloride, and the balance of the composition is medical normal saline solution; and the pH of the eyedrop is 6.5 to 7.5.

* * * * *